US011631211B2

United States Patent
Kjær-Nielsen et al.

(10) Patent No.: US 11,631,211 B2
(45) Date of Patent: Apr. 18, 2023

(54) VOLUME RENDERING USING SURFACE GUIDED CROPPING

(71) Applicant: 3SHAPE A/S, Copenhagen (DK)

(72) Inventors: Anders Kjær-Nielsen, Kastrup (DK); Adam Carsten Stoot, Søborg (DK)

(73) Assignee: 3SHAPE A/S, Copenhagen (DK)

( * ) Notice: Subject to any disclaimer, the term of this patent is extended or adjusted under 35 U.S.C. 154(b) by 0 days.

(21) Appl. No.: 16/640,168

(22) PCT Filed: Aug. 29, 2018

(86) PCT No.: PCT/EP2018/073195
§ 371 (c)(1),
(2) Date: Feb. 19, 2020

(87) PCT Pub. No.: WO2019/043038
PCT Pub. Date: Mar. 7, 2019

(65) Prior Publication Data
US 2021/0217222 A1    Jul. 15, 2021

(30) Foreign Application Priority Data
Aug. 31, 2017    (DK) .............................. PA201770656

(51) Int. Cl.
*G06T 15/08*    (2011.01)
*G06T 15/06*    (2011.01)
(Continued)

(52) U.S. Cl.
CPC ............ *G06T 15/08* (2013.01); *A61C 9/0046* (2013.01); *G06T 15/06* (2013.01); *G06T 17/00* (2013.01);
(Continued)

(58) Field of Classification Search
CPC .......... G06T 15/08; G06T 2207/30036; A61B 5/4542–4557
See application file for complete search history.

(56) References Cited

U.S. PATENT DOCUMENTS

| 6,371,761 B1 | 4/2002 | Cheang et al. |
| 9,036,881 B2 | 5/2015 | Carlson et al. |
| (Continued) | | |

FOREIGN PATENT DOCUMENTS

| CN | 103069459 A | 4/2013 |
| CN | 105916435 A | 8/2016 |
| (Continued) | | |

OTHER PUBLICATIONS

The Danish Search Report dated Feb. 7, 2018, by the Danish Patent Office in corresponding Danish Application No. PA201770656. (6 pages).

(Continued)

*Primary Examiner* — Ryan McCulley
(74) *Attorney, Agent, or Firm* — Buchanan Ingersoll & Rooney PC (57) ABSTRACT

Disclosed is surface guided cropping in volume rendering of 3D volumetric data from intervening anatomical structures in the patient's body. A digital 3D representation expressing the topography of a first anatomical structure is used to define a clipping surface or a bounding volume which then is used in the volume rendering to exclude data from an intervening structure when generating a 2D projection of the first anatomical structure.

17 Claims, 10 Drawing Sheets

(51) Int. Cl.
  *G06T 17/00* (2006.01)
  *A61C 9/00* (2006.01)
  *A61B 6/03* (2006.01)
  *A61B 6/14* (2006.01)
  *A61B 6/00* (2006.01)

(52) U.S. Cl.
  CPC .............. *A61B 6/032* (2013.01); *A61B 6/14* (2013.01); *A61B 6/5247* (2013.01)

(56) References Cited

U.S. PATENT DOCUMENTS

| | | | |
|---|---|---|---|
| 9,390,546 | B2 | 7/2016 | Buckton et al. |
| 9,474,497 | B2 | 10/2016 | Kopylov |
| 10,159,447 | B2 | 12/2018 | Klein et al. |
| 10,521,935 | B2 | 12/2019 | Ulrici |
| 2002/0037489 | A1 | 3/2002 | Jones et al. |
| 2002/0055081 | A1* | 5/2002 | Hughes ............ A61C 7/00 433/24 |
| 2009/0027385 | A1* | 1/2009 | Smith ............ G06T 13/20 345/420 |
| 2009/0220916 | A1 | 9/2009 | Fisker et al. |
| 2012/0015316 | A1 | 1/2012 | Sachdeva et al. |
| 2013/0094740 | A1 | 4/2013 | Vandenberghe |
| 2014/0227655 | A1 | 8/2014 | Andreiko et al. |
| 2015/0116323 | A1 | 4/2015 | Buckton et al. |
| 2016/0135925 | A1 | 5/2016 | Mason et al. |
| 2016/0374784 | A1 | 12/2016 | Joshi |
| 2017/0243381 | A1* | 8/2017 | Ulrici ............ A61B 6/032 |

FOREIGN PATENT DOCUMENTS

| | | |
|---|---|---|
| CN | 106572834 A | 4/2017 |
| JP | 2011083440 A | 4/2011 |
| JP | 2013536715 | 9/2013 |
| JP | 2015221217 A | 12/2015 |
| JP | 2017503244 A | 1/2017 |
| WO | 0174268 A1 | 10/2001 |
| WO | 2006031096 A1 | 3/2006 |
| WO | 2010053726 A2 | 5/2010 |
| WO | 2011133662 A1 | 10/2011 |
| WO | 2011154559 A1 | 12/2011 |
| WO | 2012028670 A1 | 3/2012 |
| WO | 2013129811 A1 | 9/2013 |

OTHER PUBLICATIONS

International Search Report (PCT/ISA/210) and Written Opinion (PCT/ISA/237) dated Nov. 15, 2018, by the European Patent Office as the International Searching Authority for International Application No. PCT/EP2018/073195.
First Office Action dated Jan. 29, 2021, by the Chinese Patent Office in corresponding Chinese Patent Application No. 2018800563440, and an English Translation of the Office Action. (17 pages).
Office Action (Communication) dated Mar. 11, 2021, by the European Patent Office in corresponding European Patent Application No. 18765392.8. (6 pages).
Office Action issued in corresponding European Patent Application No. 18 765 392.8-1122, dated Jul. 26, 2022. (6 pages).
Second Office Action issued in corresponding Chinese Patent Application No. 2018800563440 dated Sep. 27, 2021, with English Translation. (15 pages).
Notice of Reasons for Rejection issued in Japanese Patent Application No. 2020-511970; dated Aug. 9, 2022, with English Translation (8 pages).
Office Action issued in Japanese Patent Application No. 2020-511970, dated Feb. 21, 2023 (2 pages).

* cited by examiner

VOLUME RENDERING USING SURFACE GUIDED CROPPING

TECHNICAL FIELD

The disclosure generally relates to the use of surface information for cropping away unwanted or unimportant data in volume rendering of 3D volumetric data such as Computed Tomography (CT) data. The disclosure has applications within several medical fields, such as within dentistry.

BACKGROUND

Volume rendering of the 3D volumetric data can generate a 2D projection of the object as it would appear from a given viewpoint relative to the scanned object. For each different viewpoint, a new 2D projection is generated. When the volume rendering should select only 3D volumetric data relating to a particular anatomical structure, clipping planes and/or bounding boxes can be used to exclude portions of the 3D volumetric data relating to other anatomical structures. Clipping planes enclosing the 3D volumetric data that should be included in the volume rendering are then defined such that objects located outside the clipping planes are invisible in the generated 2D projection. For instance, when the volume rendering of 3D volumetric data from a patient's body interior points of a given body part can better be viewed when clipping planes are used to exclude data from portions which otherwise would block the view. U.S. Pat. No. 9,390,546 describes clipping plane in relation to removing occlusions in 3D ultrasound images.

However, often a clipping plane or a simple bounding box cannot provide a sufficiently detailed selection of 3D volumetric data relating to the selected portion, especially for occluding objects with intervening portions. When the clipping plane or bounding box cannot be arranged such that it fully separates the data relating to the selected body part the result of the rendering process either includes further portions relating to other body parts or some portions of the selected body part must be omitted.

It remains a problem to provide a highly selective volume rendering of occluding objects with intervening surfaces.

SUMMARY

Disclosed, according to an embodiment, is a method for selective volume rendering of 3D volumetric data from a patient. The method comprising:
obtaining a 3D volumetric data set comprising data for a first and a second anatomical structure in the patient's body;
obtaining a first digital 3D representation comprising a first portion expressing the topography of the first anatomical structure;
defining a first clipping surface at least partly from the first portion of the first digital 3D representation; and
generating a 2D projection of the first anatomical structure by volume rendering of the set of 3D volumetric data, where the first clipping surface is applied to exclude 3D volumetric data relating to the second anatomical structure.

Disclosed, according to an embodiment, is method for selective volume rendering of 3D volumetric data from a patient. The method comprising:
obtaining a 3D volumetric data set comprising data for a first and a second anatomical structure in the patient's body;
obtaining a first digital 3D representation comprising a first portion expressing the topography of the first anatomical structure;
defining a bounding volume at least partly from the first portion of the first digital 3D representation; and
generating a 2D projection of the first anatomical structure by volume rendering of the set of 3D volumetric data, where the bounding volume is applied to exclude 3D volumetric data relating to the second anatomical structure.

The use of a clipping surface which is not a simple plane but takes into account the shape of the first anatomical structure provides that 3D volumetric data from intervening anatomical structures can be separated in the volume rendering and that the generated 2D projection can be generated from data for the first anatomical structure only. The same is true for the use of the bounding volume taking into account the shape providing superior results compared to cases where a simple bounding box is applied in the volume rendering.

The first digital 3D representation may be obtained by any scanning technique which can provide information expressing the topography of the first anatomical structure. For a visible anatomical structure, such as teeth, a surface scanning for example using an intraoral scanner can provide the first digital 3D representation, while for an anatomical structure embedded in the patient's body the first digital 3D representation can be provided by sub-surface scanning techniques, such as Optical Coherence Tomography, ultrasound and X-ray scanning e.g. using a contrast fluid, and subsequent segmentation of recorded data.

Even though the disclosure is described mainly in terms of applications within dentistry, the described methods, computer program products and systems can be applied to any set of volumetric data where intervening surfaces of the structures where it becomes at least nearly impossible to perform a highly selective volume rendering. Likewise, the patient may be a human or an animal.

In some embodiments, the first anatomical structure comprises dental structures in a first one of the patient's jaws and the second anatomical structure comprises dental structures in the opposing second one of the patient's jaws. The dental structures in the first one of the jaws may be the jaw bone and/or at least part of the teeth of the first one of the jaws, such that the 3D volumetric data set comprises data for said jaw bone and/or teeth. The 3D volumetric data set may further comprise data for dental structures in the opposing second one of the jaws, and in particular data for the teeth in the opposing jaw. The function of the clipping surface or bounding volume disclosed herein is to exclude the data such as volumetric data relating to the dental structures in the second one of the jaws in the volume rendering providing for an improved selection of 3D volumetric data compared to prior art disclosures relying on simple clipping planes or bounding boxes.

A 3D volumetric data set obtained by X-ray scanning a patient, e.g. for planning an implant treatment, often has data for dental structures in both jaws, such as data relating to teeth and the jaw bone in the upper and lower jaws. The use of the clipping surface or bounding volume shaped according to the teeth of the first one of the jaws provides that the volume rendering generating a 2D projection of the 3D volumetric data relating to the dental structures in the first jaw efficiently can exclude volumetric data from the opposing jaw without causing that some 3D volumetric data from the first jaw are omitted in the volume rendering. I.e. when a first clipping surface defined from the first digital 3D representation is applied, the 3D volumetric data relating to dental structures of the second jaw can be excluded in the volume rendering, such that the 2D projection does not include parts from the second one of the jaws which otherwise could block the view to the first jaw in the generated 2D projection.

In some embodiments, the first digital 3D representation comprises a first surface scan and the first portion expresses the topography of one or more teeth in the first one of the patient's jaws. It is especially advantageous to take the topography of the teeth into account when the teeth are arranged in occlusion to provide that the volume rendering can select only the 3D volumetric data relating to the teeth (and jaw bone) of the selected jaw. When a simple clipping plane which ignores the topography of the teeth is used for 3D volumetric data recorded from teeth arranged in occlusion, the generated 2D projection will either include 3D volumetric data for the opposing jaw or some data from the selected jaw will not be included in the volume rendering. Taking the topography of the patient's teeth into account when defining the first clipping surface provides that even when the CT scan is recorded while the patient's mount is closed with the upper and lower jaws arranged in occlusion, the volumetric data from the opposing jaw can be excluded in the volume rendering of the first jaw. In such cases a flat clipping plane or a bounding box having only flat surfaces cannot be used to distinguish the teeth from the upper and lower jaws.

Surface scans of the patient's set of teeth can be obtained in various ways known to the skilled person, e.g. by intra oral scanning, or by scanning an impression of the teeth or a physical model of the teeth made from such an impression. The surface scan comprises topographical data expressing the topography of the teeth and has a first portion expressing the topography of one or more teeth in the part of the oral cavity for which the selective rendering is made. The portion of the first surface scan corresponding to said first part can be selected in various ways such as by using a pointer tool to indicate the first portion on a visualization of the surface scan displayed on e.g. a computer screen.

In some embodiments, the method comprises creating one or more bounding volumes arranged to enclose the 3D volumetric data included in the volume rendering, where at least part of one surface of one bounding volume is formed by the first clipping surface.

In U.S. Pat. No. 9,036,881 a modified 3D model of e.g. the teeth in one of the patient's jaws is generated by deleting 3D volumetric data relating to other parts. In some embodiments of the disclosure that instead selects which 3D volumetric data are used when generating a 2D projection by volume rendering, all available data can be maintained providing that all data still can be visualized in 2D slices along with the generated 2D projection.

The method of disclosed embodiments can also be used for avoiding scatter inducted defects in the generated 2D projection, such as defects in the 3D volumetric data caused by scattering on fillings in a patient's teeth. Instead or in addition to excluding the 3D volumetric data relating to a second anatomical structure, the scatter defects in the 3D volumetric data are excluded in the volume rendering. I.e. besides resulting in better viewing options, the disclosed cropping based on the clipping surface will also only select data from the jaw itself, and thus never show scatter defects in the occlusion or near teeth eliminating the need for CT scatter cleaning methods.

In some embodiments, the method further includes defining a second clipping surface at least partly from a second first portion of the first digital 3D representation. The second clipping surface can be used to define an opposing bounding of the selection of 3D volumetric data which are used in the volume rendering process. The second clipping surface is then arranged such that the 3D volumetric data which are included in the volume rendering are located between the two clipping planes. In dental applications, the second clipping surface may be a plane since it frequently just defines the bounding of the volume of the 3D volumetric data located away from the intervening surfaces of the occluding teeth. In some embodiments, the first and second clipping surfaces are part of a bounding volume used to select which of the 3D volumetric data are included in the volume rendering.

The 3D volumetric data may have been recorded by X-ray scanning, such as Computed Tomography (CT) X-ray or Cone beam CT (CBCT) scanning, or other scanning techniques such as MRI and OCT. In dental applications, the 3D volumetric data may comprise data for both hard and soft tissues in the oral cavity, such as the jaw bones, the gums, palette, as well as data for facial tissue, such as the patient's skin. In addition, the 3D volumetric data may include foreign objects in the oral cavity such as implants, scan posts, or any other foreign object.

In some embodiments, the volume rendering is at least partially based on ray tracing. In ray tracing rays are traced from the chosen viewpoint through the 3D volumetric data for each pixel in a virtual screen. The final pixel color is the result of accumulating (front to back) the color from each voxel that the ray intersects when moving through the volume. Any 3D volumetric data located before the first clipping surface (as seen from the viewpoint) will be excluded in the volume rendering. Similarly, will any 3D volumetric data located after the second clipping surface also be excluded. In embodiments using a bounding volume only the 3D volumetric data located within the bounding volume will be taken into account in the volume rendering.

In some embodiments, an offset is provided between the first clipping surface and the 3D volumetric data such that the first clipping surface is displaced away from the first anatomical structure. In a dental application this would correspond to displacing the first clipping surface away from the teeth in the first one of the jaws. The offset provides that 3D volumetric data relating to the first anatomical structure will not be excluded in the volume rendering even if there are slight deviations in the representation of the teeth topography given by the first digital 3D representation and the 3D volumetric data set or if there are small errors in the alignment if these.

Different embodiments of present disclosure relates to different aspects including the method, system and computer program product described above and in the following, and corresponding methods, systems and computer program products each yielding one or more of the benefits and advantages described in connection with the first mentioned aspect, and each having one or more embodiments corresponding to the embodiments described in connection with the first mentioned aspect and/or disclosed in the appended claims.

Disclosed, according to an embodiment, is a computer program product comprising computer instructions for causing a data processor unit to perform the method according to any of the embodiments when said computer instructions are executed on the data processing unit. The computer program product may be embedded on a non-transitory computer readable medium.

Disclosed, according to an embodiment, is a non-transitory computer readable medium encoded with a computer program product comprising computer instructions for causing a data processor unit to perform the method according to any of the embodiments when said computer instructions are executed on the data processor unit.

Disclosed, according to an embodiment, is a system comprising a data processor unit and a non-transitory computer readable medium encoded with a computer program product comprising computer instructions for causing the data processor unit to perform the method according to any of the embodiments when said computer instructions are executed on the data processor unit.

Disclosed, according to an embodiment, is a method for selective volume rendering of 3D volumetric data from a patient, the method comprising:
  obtaining 3D volumetric data set comprising data for dental structures in a first one of the patient's jaws and data for dental structures in the opposing second one of the jaws;
  obtaining a first surface scan comprising a first portion expressing the topography of one or more teeth in the first one of the patient's jaws;
  defining a first clipping surface at least partly from the first portion of the first surface scan; and
  generating a 2D projection of the dental structures in the first one of the jaws by volume rendering of the set of 3D volumetric data, where the first clipping surface is applied to exclude 3D volumetric data relating to dental structures of the second jaw.

Disclosed, according to an embodiment, is a method for selective volume rendering of 3D volumetric data from a patient, the method comprising:
  obtaining 3D volumetric data set comprising data for dental structures in a first one of the patient's jaws and data for dental structures in the opposing second one of the jaws;
  obtaining a first surface scan comprising a first portion expressing the topography of one or more teeth in the first one of the patient's jaws;
  defining a bounding volume having a first clipping surface shaped at least partly by the first portion of the first surface scan; and
  generating a 2D projection of the dental structures in the first one of the jaws by volume rendering of the set of 3D volumetric data, where the bounding volume is applied to select the volumetric data included in the volume rendering such that 3D volumetric data relating to dental structures of the second jaw are excluded.

BRIEF DESCRIPTION OF THE DRAWINGS

The above and/or additional objects, features and advantages of the present disclosure, will be further elucidated by the following illustrative and non-limiting detailed description of embodiments of the present disclosure, with reference to the appended drawings, wherein.

DETAILED DESCRIPTION

In the following description, reference is made to the accompanying figures, which show by way of illustration how the disclosure may be practiced.

Figure 1:
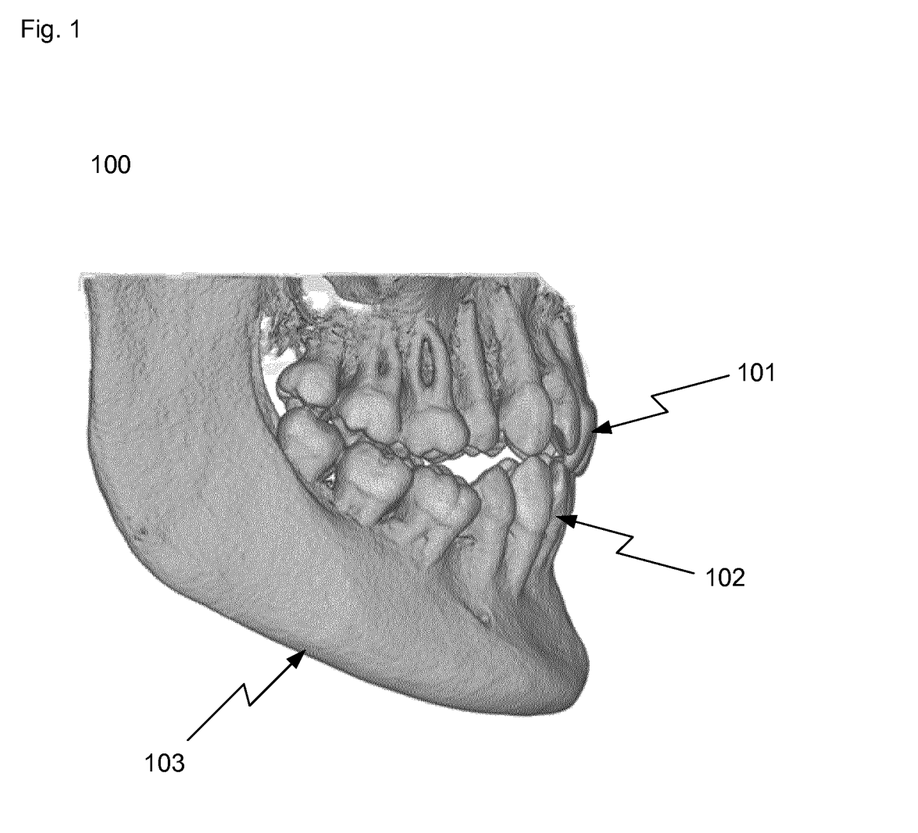
FIG. 1 shows a 2D projection of 3D volumetric data recorded from a patient according to an embodiment.

FIG. 1 shows a 2D projection of 3D volumetric data recorded from a patient by Computed tomography (CT) X-ray scanning according to an embodiment. Computed tomography, particularly x-ray computed tomography, is a widely used volumetric imaging principle. In general terms, a radiation source and a radiation-sensitive image sensor are arranged on a line, with the subject of the examination positioned in between. The subject attenuates the radiation. The source-detector arrangement is typically moved into several positions, often on a circle or segment thereof, around the subject of the examination, and images are taken at every position. A 3D volumetric data set expressing the spatial, volumetric distribution of the attenuation coefficient within the subject can then be generated from the recorded images. CT scanning of a patient's set of teeth is commonly used to extract information regarding the structure of the patient's dental structures, such as teeth topography and jaw bone densities. The CT data may relate both to outer surfaces of the teeth or internal structures such as teeth roots or nerves.

The 3D volumetric data 100 illustrated in FIG. 1 has data for the maxillary teeth 101 (i.e. the teeth in the upper jaw), for the mandibular teeth 102 (i.e. the teeth in the lower jaw) and for the mandibular jaw bone 103. The 3D volumetric data are provided as a grid of voxels each having a CT number value relating to the attenuation of the X-rays in the material for the corresponding position in the scanned volume. The CT number is given by:

$$\text{CT number} = K * (u_{voxel} - u_{water}) / u_{water}$$

where $u_{voxel}$ and $u_{water}$ are the calculated voxel attenuation coefficient and the attenuation coefficient of water, respectively, and K is an integer constant. The 2D projection is generated using ray tracing where rays are traced from the chosen viewpoint through the 3D volumetric data for each pixel in a virtual screen. The final pixel color is the result of accumulating (front to back) the color from each voxel that the ray intersects when moving through the volume. To determine the color of each voxel a color function is used, which translates the voxel "intensity" to a color. Using such a color function allows for air voxels to be regarded as (semi-)transparent, as well as assigning the desired colors to, e.g., skin, bone and teeth.

The CT data may e.g. be acquired for planning the position of an implant in the patient's lower jaw and the operator wishes to view a volume rendering of the data from teeth and jaw bone in this jaw only. Commercially available software for handling volume rendering of CT scan data often allow the operator to select a volume for the rendering. This volume can be indicated by clipping planes clipping through the scan data relating to the upper and lower jaws and/or a simple bounding box enclosing the relevant volume.

When the CT data are recorded while the patient's teeth are in occlusion, such a bounding box or clipping plane cannot provide the correct separation of data for many patients. This may be with respect to the anterior teeth where the upper anterior teeth extend below the occlusal surfaces of several teeth in the lower jaw. Or at the occlusal surfaces of several or the pre-molar or molar teeth, where often no clipping plane which fully separates the occlusal surfaces of the teeth in the upper and lower jaws can be defined.

FIG. 2 illustrates the problem that may occur when attempting to separate 3D volumetric data relating one jaw from data relating to the opposing jaw using a simple clipping plane. In this example, the objective is to generate a 2D projection of the 3D volumetric data for the lower jaw, but the encountered problem would evidently also occur if the objective was to select data from the upper jaw only.

Figure 2A:
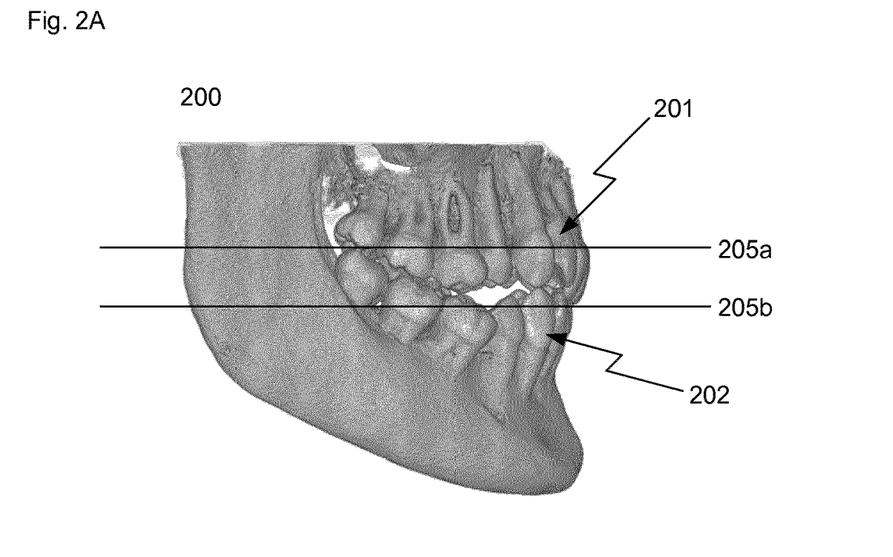
FIGS. 2A-2D illustrate a prior art method for separating 3D volumetric data relating to the two jaws.
Figure 2B:
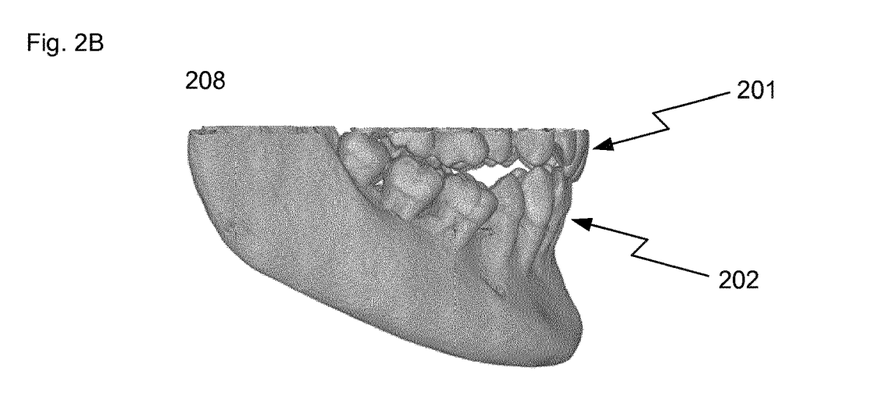

In FIG. 2A, the horizontal lines 205a and 205b are both cross sectional representations of a clipping plane extending into the plane of the figure. Considering initially the result of a volume rendering based on a clipping plane arranged according to line 205a it can be seen in FIG. 2B that this arrangement provides that all 3D volumetric data relating to the teeth and jaw bone of the lower jaw are included in the 2D projection 208. However, as also seen the 3D volumetric data relating to the teeth 201 in the opposing jaw are also included in the generated 2D projection blocking the visual access to some surfaces of the teeth 202 in the lower jaw.

Figure 2C:
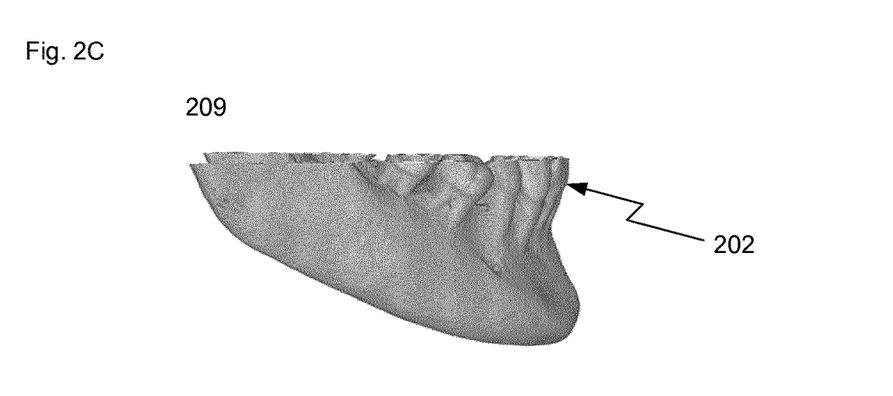
Figure 2D:
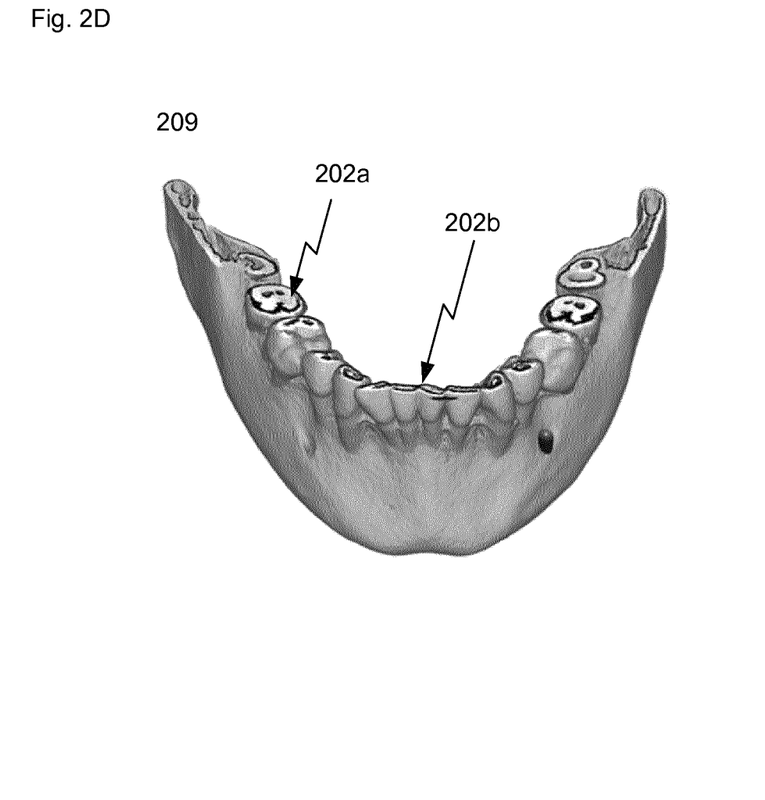

FIGS. 2C and 2D show a 2D projection generated by volume rendering of the 3D volumetric data 200 applying a first clipping plane according to line 205b. FIG. 2C shows the 2D projection generated when the viewpoint is from the side of the patent, while FIG. 2D shows it when the viewpoint is in front of the patient's face. The first clipping plane according to line 205b is arranged such that all 3D volumetric data relating to the teeth in the upper jaw are located above the clipping plane. Applying such a clipping plane in the volume rendering thus ensures that the teeth of the opposing jaw does not block the visual access to the teeth 202 of the lower jaw. However, as also illustrated in FIGS. 2C and 2D, the generated projection does not include volumetric data for the occlusal and incisal surfaces of the posterior and 202a anterior teeth 202b of the lower jaw, respectively.

Figure 3:
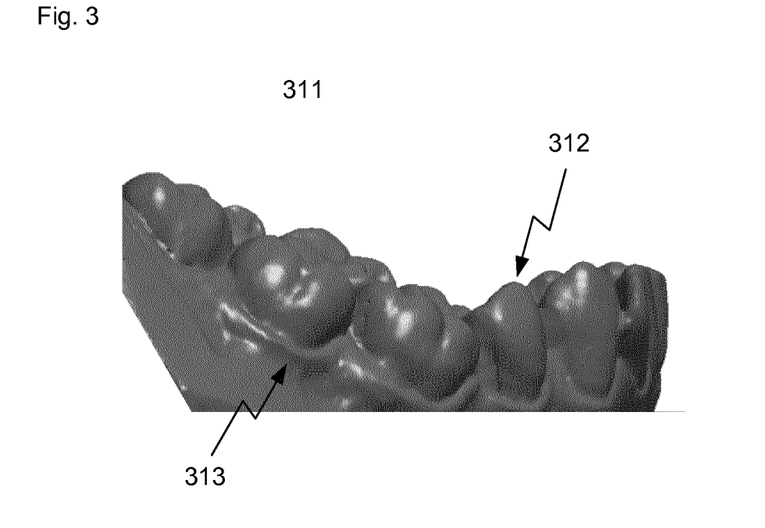
FIG. 3 shows data from a surface scan according to an embodiment.

FIG. 3 shows visual representation of a surface scan of the teeth in the lower jaw according to an embodiment.

The surface scan 311 illustrated in FIG. 3 has teeth data 312 expressing the topography of the teeth and gingiva data 313 for the gingiva in the lower jaw. The surface scan can be recorded for example using an intraoral scanner, such as the TRIOS scanner manufactured by 3Shape A/S.

Figure 4A:
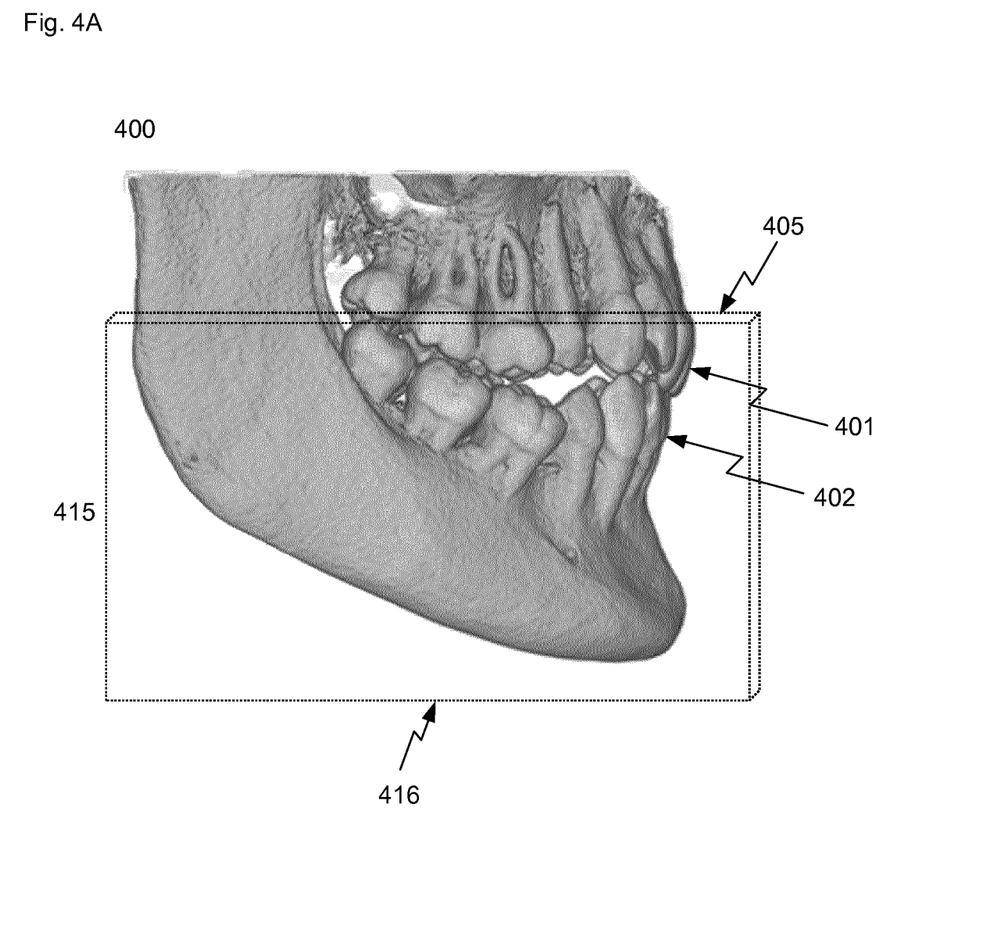
FIGS. 4A-4C illustrate how a bounding volume can be defined from a structured clipping surface according to an embodiment.
Figure 4B:
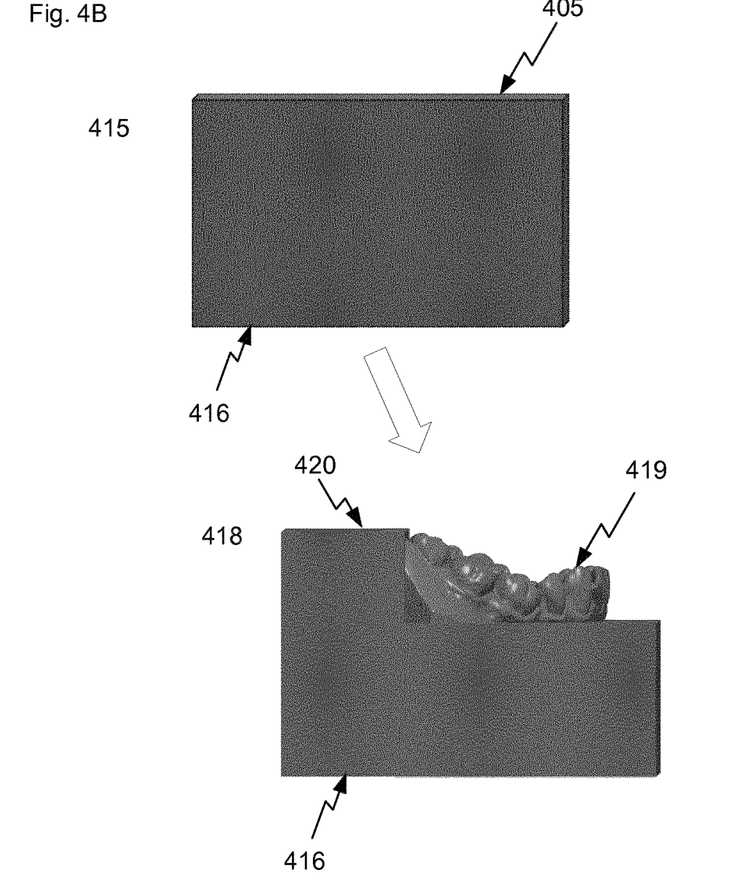
Figure 4C:
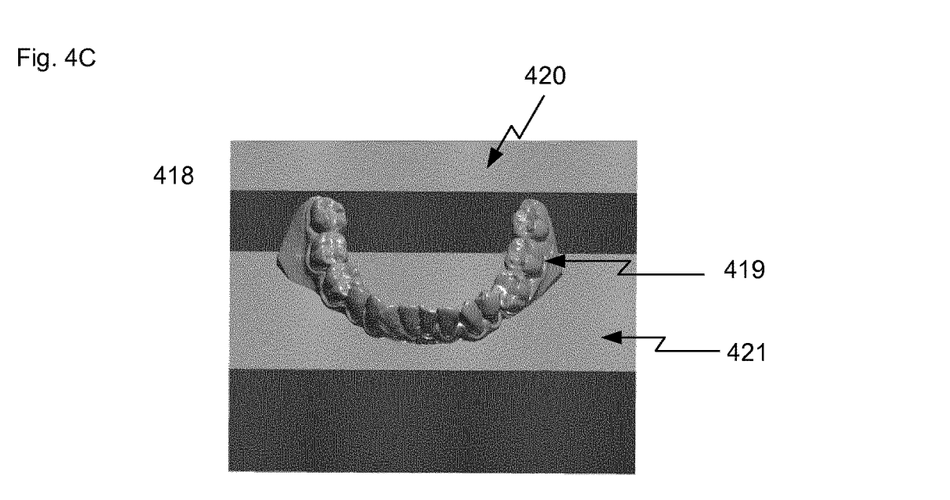

FIG. 4 illustrates how a bounding volume with a structured clipping surface can be used to provide a more selective volume rendering according to an embodiment.

FIG. 4A shows the 3D volumetric data 400 and a simple bounding box 415 defining the portion of the 3D volumetric data which are to be used in a volume rendering. The bounding box 415 has a first clipping surface 405 and a second clipping surface 416.

The first clipping surface is planar and is arranged like the first clipping plane 205a illustrated in FIG. 2A. As also illustrated in FIG. 2 this arrangement of the first clipping surface provides that some 3D volumetric data for the teeth of the upper jaw will be included in the volume rendering.

FIG. 4B illustrates how bounding volume created by modifying the simple bounding 415 to have a first clipping surface defined from a surface scan of the teeth in the lower jaw. The bounding box is modified by replacing a part of the first clipping plane with the surface scan such that the first clipping surface of the bounding volume 418 has a section 419 shaped according to the topography of the patient's teeth and behind that a section 420 which is maintained and provide that the part of the jaw bone located behind the teeth can be included in the volume rendering.

The bounding volume 418 with the tooth structured first clipping surface is also depicted in FIG. 4C showing the tooth shaped part 419, the maintained section 420, and the section 421 surrounding the tooth shaped part.

The structured first clipping surface which at least in one region is shaped according to the topography of the first portion of the teeth has the advantage that the volume rendering more precisely can select the appropriate 3D volumetric data for the volume rendering as described below in relation to FIG. 5.

Figure 5A:
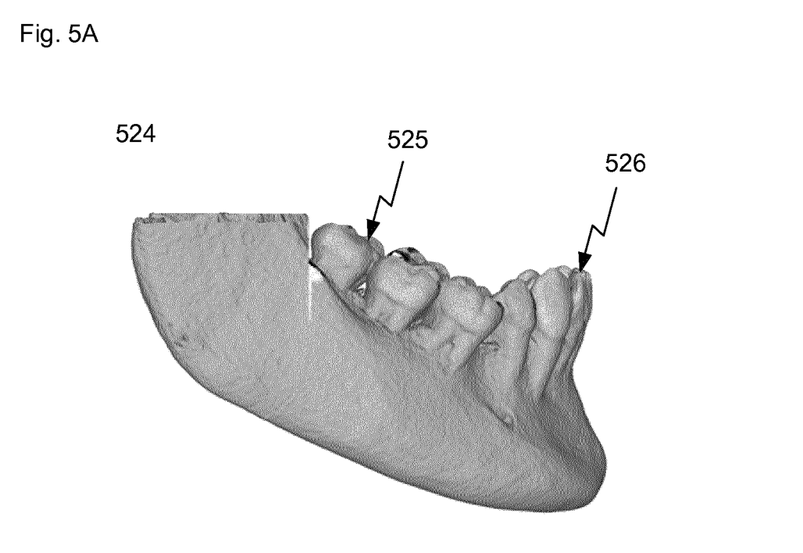
FIGS. 5A-5C show 2D projections of the 3D volumetric data with the improved selectivity according to an embodiment.
Figure 5B:
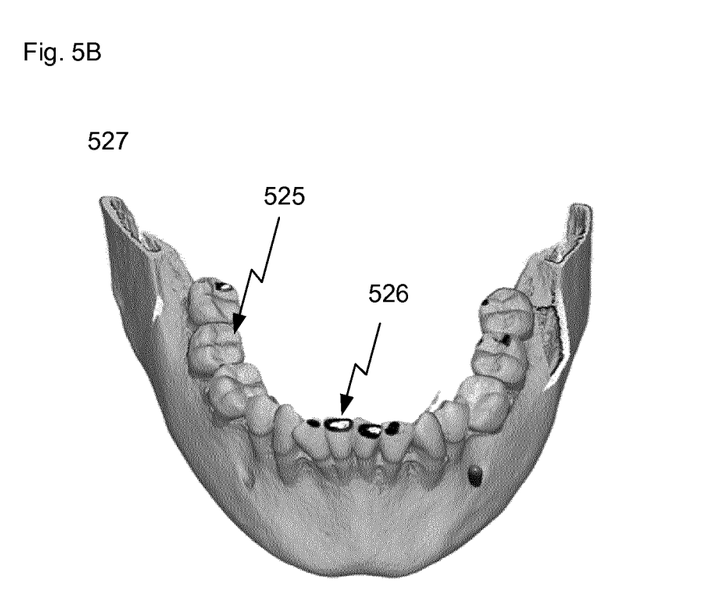
Figure 5C:
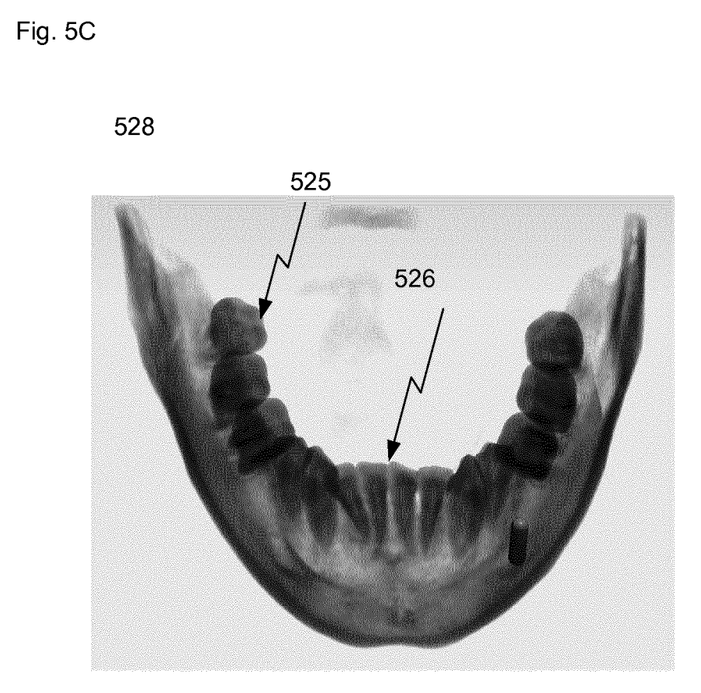

FIG. 5 shows 2D projections of the 3D volumetric data with the improved selectivity according to an embodiment.

FIGS. 5A and 5B show 2D projections of the 3D volumetric data when the bounding volume takes the topography of the teeth into account when cropping the 3D volumetric data. The bounding volume with the structured first clipping surface illustrated in FIGS. 4B and 4C is used when these 2D projections are generated.

In FIG. 5A, the 2D projection 524 shows the rendered 3D volumetric data as seen from a viewpoint located at the side of the patient's face. A comparison between this 2D projection and the 2D projections seen in FIGS. 2B and 2C (where a bounding box with a simple planar first clipping surface was used) illustrates how the teeth-shaped first clipping surface provides a cropping with a highly selective volume rendering of the 3D volumetric data relating to the lower jaw. The improved selection of 3D volumetric data provides that the occlusal surfaces of the posterior teeth 525 can be included in a 2D projection where the incisal surfaces of the anterior teeth 526 are seen without the volumetric data from the opposing upper jaw interfering in the view.

The improvement is also clearly seen in the 2D projection 527 of FIG. 5B which shows a 2D projection of the volume rendered 3D volumetric data as seen from a viewpoint located in front of the patient's face. This 2D projection should be compared with that illustrated in FIG. 2D and the use of the improved first clipping plane evidently provides for a higher selectivity when volume rendering the 3D volumetric data such that the occlusal surfaces of the posterior teeth 525 can be included in the 2D projection 527 and the incisal surfaces of the anterior teeth 526 can be seen free of the volumetric data from opposing upper jaw interfering in the view.

FIG. 5C shows a 2D projection generated using threshold values for the different types of tissue, i.e. jaw bone, dentine and enamel of the teeth which provide that the 2D projection also expresses the internal structure of the teeth in the lower jaw. This confirm that the rendered 3D volumetric data still includes data for these internal structures which is one of the advantages of the disclosed method over prior art approaches in which a new 3D model is generated by deleting volumetric data not relating to the surface of the teeth. In the disclosed method where a new 2D projection is generated for each viewpoint by volume rendering, all 3D volumetric data are maintained, the selection only relates to which data are included in the volume rendering.

Figure 6:
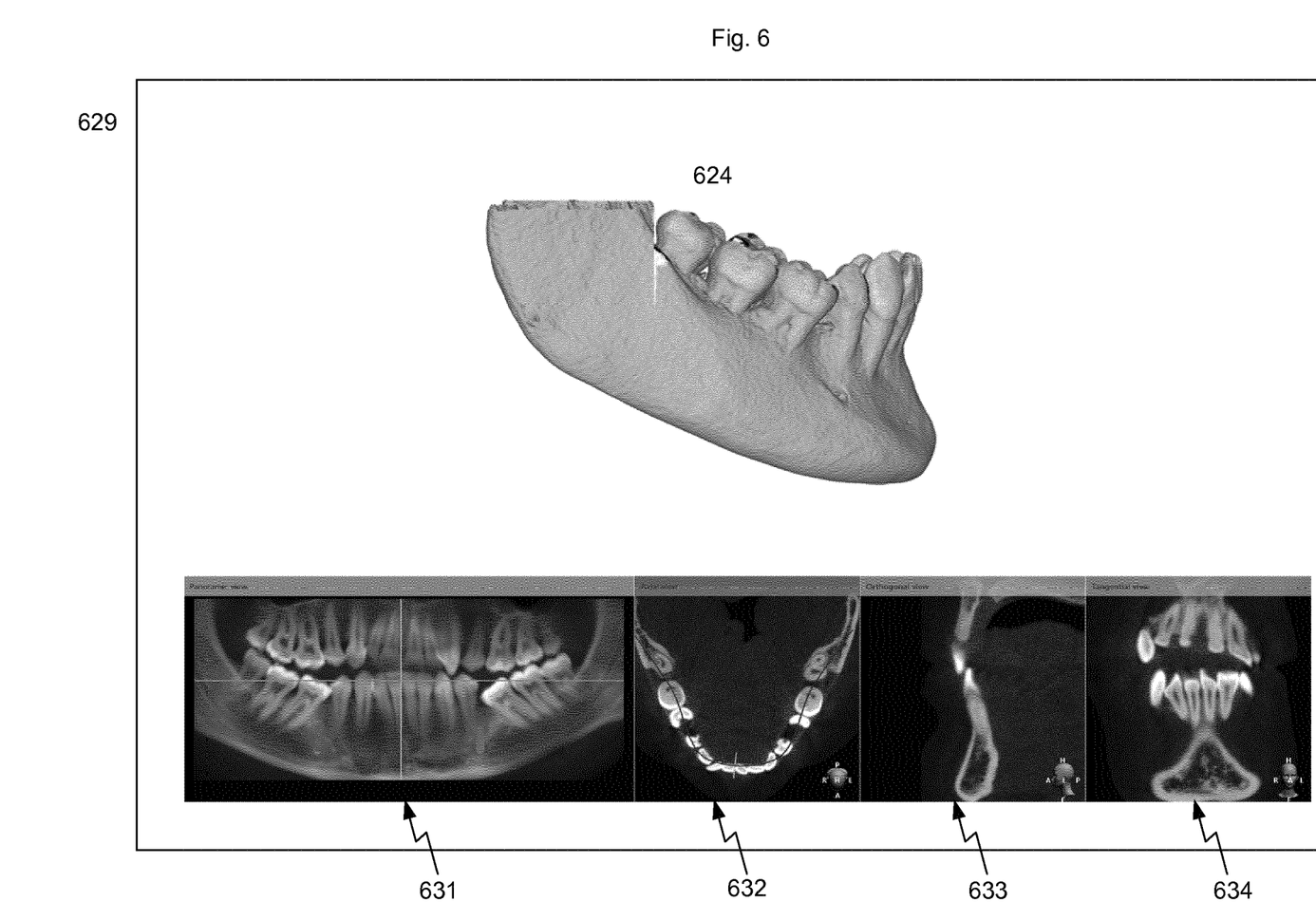
FIG. 6 shows a 2D projection of the 3D volumetric data with the improved selectivity according to an embodiment.

FIG. 6 shows parts of a user interface 629 configured for viewing 3D volumetric data recorded from a patient according to an embodiment.

The 2D projection 624 is generated by using the improved first clipping plane in the volume rendering to select 3D volumetric data relating to dental structures in the lower jaw only. In addition to displaying the 2D projection, the user interface also shows a panoramic view 631 and three 2D slices providing an axial view 632, an orthogonal view 633 and a tangential view 634 of the 3D volumetric data set. This Figure illustrates that the disclosed method provides the advantage that all 3D volumetric data are maintained and can be represented in different views 631, 632, 633 and 634 together with the generated 2D projection 624.

Figure 7:
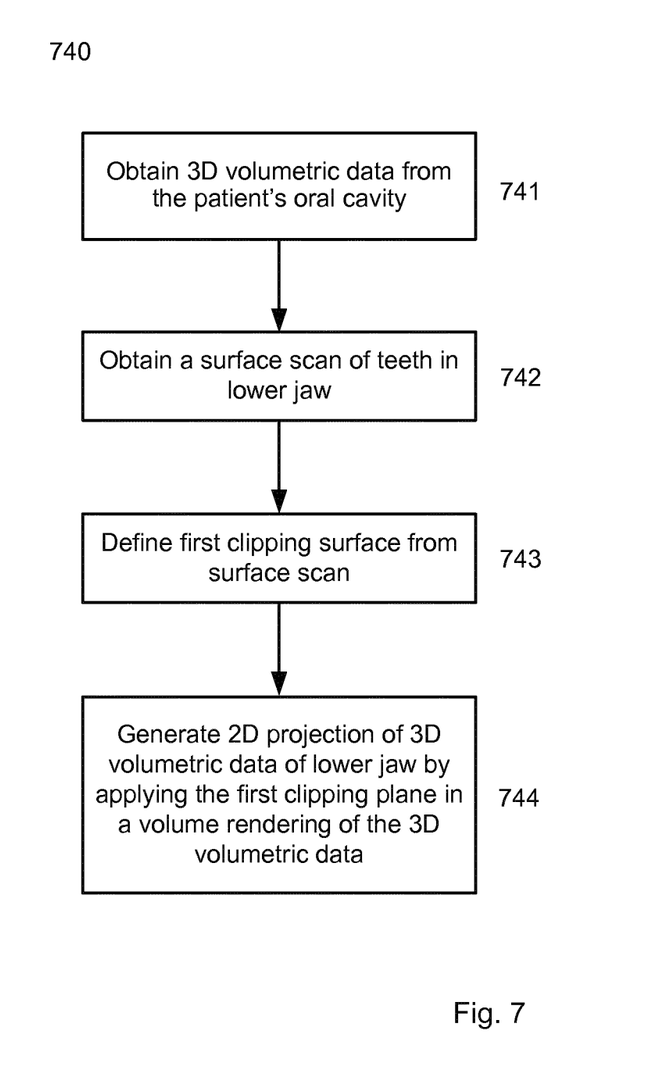
FIG. 7 shows steps according to an embodiment.

FIG. 7, according to an embodiment, shows a flowchart 740 with steps of the method when applied to selectively volume render 3D volumetric data from the patient's lower jaw, i.e. where a cropping provides that data from the upper jaw are excluded in the volume rendering.

In step 741 a 3D volumetric data set of the patient's teeth and jaw bones is obtained. The 3D volumetric data may be provided by X-ray Computed Tomography scanning and loaded into a microprocessor of a data processing system configured for implementing the method.

In step 742 a surface scan of teeth in lower jaw is obtained, e.g. by intra oral scanning using a TRIOS scanner supplied by 3Shape A/S and loaded into the microprocessor. The surface scan comprises data expressing the topography of the teeth in the lower jaw.

In step 743 a first clipping surface is defined from the obtained surface scan. The first clipping surface can be defined part of a bounding volume and formed by replacing a portion of a bounding box with the surface scan as illustrated in FIG. 4B above. The surface scan or the defined clipping surface is oriented and resized to have the same scale and orientation as the 3D volumetric data such that the teeth surfaces on the surface scan are aligned with the corresponding 3D volumetric data. The alignment can be performed using an Iterative Closest Point algorithm to minimize the difference between the surface scan and the corresponding part of the 3D volumetric data, by detecting corresponding points in the surface scan and 3D volumetric data and aligning these points, or by a manual process.

In Step 744 a 2D projection of 3D volumetric data of lower jaw is generated by applying the first clipping plane in a volume rendering of the 3D volumetric data. When the first clipping surface is part of a bounding volume, the bounding volume is arranged such that the first clipping surface follows the teeth while the second clipping surface of the volume is located opposite to the volumetric data of the lower jaw.

Figure 8:
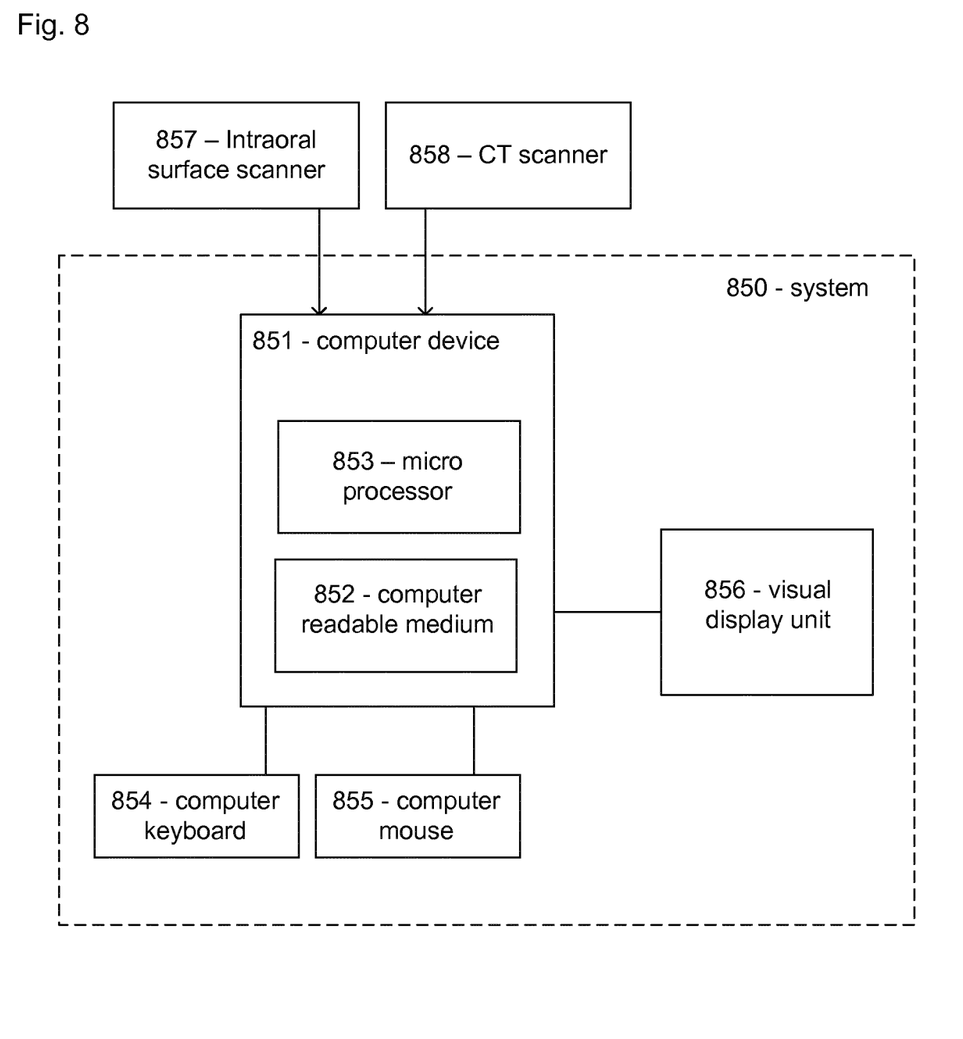
FIG. 8 illustrates a system according to an embodiment.

FIG. 8, according to an embodiment, shows a schematic of a system according to an embodiment where a selective volume rendering of 3D volumetric data from a patient's set of teeth is based on an intraoral scan of the teeth. The system 850 comprises a computer device 851 comprising a computer readable medium 852 and an electronic data processing device in the form of a microprocessor 853. The system further has a visual display unit 856, and at least one access device and/or interface that allow the operator to utilize the functionality of the computer system and for entering data and activating virtual buttons of a user interface visualized on the visual display unit 856. The access device and/or interface can include but is not limited to a keyboard, mouse, touch screen, stylus, joystick, light pen, trackball, voice interactive function, three-dimensional glove, solid three-dimensional mouse ball, graphical user interface (GUI), display screen, printer, and other known input or output devices and interfaces. In FIG. 8 the access devices are a computer keyboard 854 and a computer mouse 855. The visual display unit 856 can e.g. be a computer screen. The computer may be a general purpose computer capable of running a wide variety of different software applications or a specialized device limited to particular functions. The computer may include any type, number, form, or configuration of processors, system memory, computer-readable mediums, peripheral devices, and operating systems. The computer may include a personal computer (PC), which may be in the form of a desktop, laptop, tablet PC, or other known forms of personal computers.

The computer device 851 can receive both a surface scan and a 3D volumetric data set of the patient's teeth which both can be stored in the computer readable medium 852 and loaded to the microprocessor 853 for processing. The surface scan can be obtained as a digital 3D representation of the teeth recorded for example using an intraoral scanner 857, such as the TRIOS 3 intra-oral scanner manufactured by 3Shape TRIOS A/S. The 3D volumetric can be recorded using e.g. a cone beam CT scanner 858.

A computer program product with computer instructions for causing the microprocessor to perform several of the steps of the inventive method is stored on the non-transitory computer readable medium 852. For example, the computer program product can have algorithms for manipulating and aligning surface scan and 3D volumetric data set, and for performing the ray tracing used in the volume rendering to produce the 2D projection. The computer system provides for the execution of the method steps by which the obtained can be, either automatically or in response to operator commands.

In case of a user assisted alignment of the surface scan and the 3D volumetric data, the system 850 provides that an operator can arrange the surface scan and the 3D volumetric data according to the spatial arrangement which best reflects to anatomical correct arrangement using e.g. a computer mouse to drag or rotate visualizations of the surface scan and the 3D volumetric data on the visual display unit 856. When the operator is satisfied with the relative arrangement he activates a virtual push button in the user interface and the spatial relationship is stored in the computer readable medium 852. The computer readable medium 852 can also have instructions for performing the alignment automatically, e.g. such as ICP based algorithms.

Although some embodiments have been described and shown in detail, the disclosure is not restricted to them, but may also be embodied in other ways within the scope of the subject matter defined in the following claims. In particular, it is to be understood that other embodiments may be utilized and structural and functional modifications may be made without departing from the scope of the present disclosure.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for selective volume rendering of 3D volumetric data from a patient, the method comprising:
   obtaining a 3D volumetric data set comprising data for a first and a second anatomical structure in the patient's body, wherein an occlusal surface of the first anatomical structure has a topography surface;
   obtaining a first digital 3D representation comprising a first portion of a surface scan of the topography surface of the occlusal surface of the first anatomical structure;
   defining a bounding box having a first clipping surface and a second clipping surface, the bounding box defining a portion of the 3D volumetric data set to be used in volume rendering;
   replacing the first clipping surface at least partly with the topography surface of the occlusal surface of the first anatomical structure, wherein the topography surface that replaced the first clipping surface is generated only from the surface scan of the first digital 3D representation; and
   generating a 2D projection of the first anatomical structure by volume rendering of the set of 3D volumetric data defined by the bounding box, where the first clipping surface is applied to exclude 3D volumetric data relating to the second anatomical structure, wherein the 2D projection is generated only from the 3D volumetric data set.

2. The method according to claim 1, wherein the first anatomical structure comprises dental structures in a first one of the patient's jaws and the second anatomical structure comprises dental structures in the opposing second one of the patient's jaws.

3. The method according to claim 2, wherein the first digital 3D representation expresses the topography of one or more teeth in the first one of the patient's jaws.

4. The method according to claim 1, wherein the anatomical structures comprise a jaw bone or at least part of teeth of the first one of the anatomical structures.

5. The method according to claim 1, wherein the method comprises creating a bounding volume arranged to enclose the 3D volumetric data included in the volume rendering, where at least part of one surface of the bounding volume is formed by the first clipping surface.

6. The method according to claim 1, wherein the volume rendering at least partially is based on ray tracing.

7. The method according to claim 1, wherein an offset is provided between the first clipping surface and the 3D volumetric data such that the first clipping surface is displaced away from the first anatomical structure.

8. The method according to claim 1, wherein the first anatomical structure comprises a plurality of dental structures in a first one of the patient's jaws and the second anatomical structure comprises a plurality of dental structures in the opposing second one of the patient's jaws.

9. The method according to claim 1, wherein an offset is provided between the first clipping surface and the 3D volumetric data such that the first clipping surface is displaced away from teeth in the first anatomical structure.

10. The method according to claim 1, wherein the 3D volumetric data set is obtained from a first data set and the first digital 3D representation is obtained from a second data set.

11. The method of claim 1, further comprising defining a first clipping surface at least partly from the first portion of the surface scan of the topography surface of the occlusal surface of the first anatomical structure.

12. The method of claim 11, further comprising orienting and resizing the defined first clipping surface to have a same scale and orientation as the 3D volumetric data set.

13. A method for selective volume rendering of 3D volumetric data from a patient, the method comprising:
   obtaining a 3D volumetric data set comprising data for a first and a second anatomical structure in the patient's body, wherein an occlusal surface of the first anatomical structure includes a topography surface;
   subsequently obtaining a first digital 3D representation comprising a first portion of a surface scan of the topography surface of the occlusal surface of the first anatomical structure;
   defining a bounding volume using at least the topography surface of the occlusal surface of the first digital 3D representation, wherein the topography surface is generated only from the surface scan of the first digital 3D representation; and
   generating a 2D projection of the first anatomical structure by volume rendering of the set of 3D volumetric data, where the bounding volume is applied to exclude 3D volumetric data relating to the second anatomical structure, wherein the 2D projection is generated only from the 3D volumetric data set.

14. The method according to claim 13, wherein the first anatomical structure comprises a plurality of dental structures in a first one of the patient's jaws and the second anatomical structure comprises a plurality of dental structures in the opposing second one of the patient's jaws.

15. The method according to claim 13, wherein the 3D volumetric data set is obtained from a first data set and the first digital 3D representation is obtained from a second data set.

16. The method of claim 13, further comprising defining a first clipping surface at least partly from the first portion of the surface scan of the topography surface of the occlusal surface of the first anatomical structure.

17. The method of claim 16, further comprising orienting and resizing the defined first clipping surface to have a same scale and orientation as the 3D volumetric data set.

* * * * *